(12) United States Patent
Hartzell et al.

(10) Patent No.: US 8,232,109 B2
(45) Date of Patent: *Jul. 31, 2012

(54) MICRO-PIXELATED ACTIVE-MATRIX FLUID-ASSAY PERFORMANCE

(75) Inventors: John W. Hartzell, Camas, WA (US); Pooran Chandra Joshi, Vancouver, WA (US); Paul J. Schuele, Washougal, WA (US); Andrei Gindilis, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 740 days.

This patent is subject to a terminal disclaimer.

(21) Appl. No.: 11/888,491

(22) Filed: Jul. 31, 2007

(65) Prior Publication Data

US 2008/0085559 A1 Apr. 10, 2008

Related U.S. Application Data

(60) Provisional application No. 60/849,875, filed on Oct. 6, 2006.

(51) Int. Cl.
*G01N 21/00* (2006.01)
(52) U.S. Cl. ............. 436/164; 436/2; 436/805; 385/15; 385/17; 435/289.1; 435/287.1; 435/288.5; 422/68.1; 422/82.05
(58) Field of Classification Search ............... None
See application file for complete search history.

(56) References Cited

U.S. PATENT DOCUMENTS

| | | | |
|---|---|---|---|
| 5,143,854 A | 9/1992 | Pirrung et al. | |
| 5,514,501 A | 5/1996 | Tarlov | |
| 6,093,302 A | 7/2000 | Montgomery | |
| 6,197,503 B1 | 3/2001 | Vo-Dinh et al. | |
| 6,280,595 B1 | 8/2001 | Montgomery | |
| 6,403,317 B1 | 6/2002 | Anderson | |
| 6,551,784 B2 * | 4/2003 | Fodor et al. | 506/9 |
| 6,605,796 B2 | 8/2003 | Brandinger et al. | |
| 6,731,831 B2 | 5/2004 | Tu | |
| 6,794,052 B2 * | 9/2004 | Schultz et al. | 506/20 |
| 6,860,939 B2 | 3/2005 | Hartzell | |

(Continued)

FOREIGN PATENT DOCUMENTS

JP 2004-001200 8/2004

(Continued)

OTHER PUBLICATIONS

Arntz et al. 2003. "Label-free protein assay based on a nanomechanical cantilever array." *Nanotechnology*. 14:86-90 (5 pp).

(Continued)

*Primary Examiner* — Sally Sakelaris
(74) *Attorney, Agent, or Firm* — David C. Ripma, Esq.; Jon M. Dickinson, Esq.

(57) ABSTRACT

A method of performing a fluid-material assay employing a device including at least one active pixel having a sensor with an assay site functionalized for selected fluid-assay material. The method includes exposing the pixel's sensor assay site to such material, and in conjunction with such exposing, and employing the active nature of the pixel, remotely requesting from the pixel's sensor assay site an assay-result output report. The method further includes, in relation to the employing step, creating, relative to the sensor's assay site in the at least one pixel, a predetermined, pixel-specific electromagnetic field environment.

4 Claims, 6 Drawing Sheets

U.S. PATENT DOCUMENTS

| | | | |
|---|---|---|---|
| 6,985,655 B2 | 1/2006 | Yamamoto | |
| 7,125,451 B2 | 10/2006 | Hartzell | |
| 7,128,783 B2 | 10/2006 | Hartzell | |
| 7,135,070 B2 | 11/2006 | Hartzell | |
| 7,156,916 B2 | 1/2007 | Hartzell | |
| 7,163,822 B2 * | 1/2007 | Yazawa et al. | 435/287.2 |
| 2003/0035109 A1 | 2/2003 | Hartwich et al. | |
| 2003/0219196 A1 * | 11/2003 | Weng et al. | 385/17 |
| 2005/0063870 A1 * | 3/2005 | Fukushima et al. | 422/82.05 |
| 2007/0072169 A1 * | 3/2007 | Peyvan et al. | 435/4 |

FOREIGN PATENT DOCUMENTS

| | | |
|---|---|---|
| WO | WO 9210092 | 6/1992 |

OTHER PUBLICATIONS

Jacobson et al. 1985. "Functionalized Congeners of Adenosine: Preparation of Analogues with High Affinity for $A_1$-Adenosine Receptors" *J. Med. Chem.* 28:1341 (1 p, abstract only).

McGall, et al., Jun. 4, 1997, *Journal of the American Chemical Society*, 119(22).

Noda et al. "Development of Photolithography System with Liquid Crystal Device as Active Mask for Synthesizing DNA Chips", Proceedings of the Japan Society of Mechanical Engineers, Kanto Branch, the Japan Society for Precision Engineering, Ibaraki Conference, 2003, vol. 2003, p. 201-202. Japan, Only Abstract in English.

USPTO Office Action, U.S. Appl. No. 11/827,173, dated Nov. 27, 2009, 14 pages total.
USPTO Office Action, U.S. Appl. No. 11/827,173, dated May 21, 2010, 9 pages total.
USPTO Office Action, U.S. Appl. No. 11/827,173, dated Dec. 8, 2010, 10 pages total.
USPTO Office Action, U.S. Appl. No. 11/827,335, dated Mar. 15, 2010, 20 pages total.
USPTO Office Action, U.S. Appl. No. 11/827,335, dated Aug. 11, 2010, 16 pages total.
USPTO Office Action, U.S. Appl. No. 11/827,175, dated Jan. 3, 2011, 13 pages total.
USPTO Office Action, U.S. Appl. No. 11/827,174, dated Dec. 3, 2010, 14 pages total.
USPTO Office Action, U.S. Appl. No. 11/827,176, dated Jan. 3, 2011, 14 pages total.
USPTO Office Action, U.S. Appl. No. 11/827,173, dated Apr. 8, 2011, 11 pages total.
USPTO Office Action, U.S. Appl. No. 11/827,335, dated Apr. 12, 2011, 13 pages total.
USPTO Office Action, U.S. Appl. No. 11/827,175, dated May 31, 2011, 11 pages total.
USPTO Office Action, U.S. Appl. No. 11/827,174, dated Apr. 11, 2011, 14 pages total.
USPTO Office Action, U.S. Appl. No. 11/827,176, dated May 31, 2011, 10 pages total.

* cited by examiner

MICRO-PIXELATED ACTIVE-MATRIX FLUID-ASSAY PERFORMANCE

CROSS REFERENCE TO RELATED APPLICATION

This application claims filing-date priority to currently U.S. Provisional Patent Application Ser. No. 60/849,875, filed Oct. 6, 2006, for "Micro-Pixelated Array Assay Structure and Methodology". The entire disclosure content of that prior-filed provisional case is hereby incorporated herein by reference.

BACKGROUND AND SUMMARY OF THE INVENTION

This invention relates to the field of fluid-material assays. More particularly, it relates to the performance of such an assay in the specific context of employing a significantly improved type of thin-film-based, active-pixel, pixelated assay-response matrix of the kind illustrated and described both in the above-mentioned provisional application, and also in currently co-pending U.S. patent application Ser. No. 11/827,174, filed Jul. 10, 2007, for "Micro-Pixelated Fluid-Assay Structure", the full disclosure content of which is hereby incorporated herein by reference.

This active-pixel matrix, which is a digitally accessible and controllable structure linkable to a suitable digital computer, offers a very high degree of controlled, assay-response, pixel-specific sensitivity with respect to which an assay response (a) can be output-read on a precision, pixel-by-pixel basis, and (b) can additionally be examined along uniquely accessible, special, plural and freely selectable, independent-variable "information-gathering axes", such as a time-based axis, and an electromagnetic-field-variable (light, heat, non-uniform electrical) axis.

This matrix structure with its included electronically active pixels, which structure is preferably employed in the assay-performance practice of the present invention, is formed conveniently on a low-temperature substrate material, such as glass, and may involve, in its underlying construction, low-temperature, internal crystalline-structural processing of a material, such as amorphous silicon, to create some of its pixel-borne structural features. Such crystalline-structural processing is described in U.S. Pat. No. 7,125,451 B2, the disclosure content of which patent is also hereby incorporated herein by reference.

More will be stated below herein regarding the interesting features of this representative matrix structure which make it so conveniently useable in the practice of the present invention.

So as to describe fully the important practice aspects of the present method invention, those practice aspects are illustrated and discussed herein in relation to a specific form of pixelated matrix device—the form particularly set forth in depth in the '174 patent application. It should be understood, and it will become apparent, that other device forms may be employed, so long as these other forms include and display certain important structural and behavioral features principally focused on the possession of what are referred to herein as individually, digitally computer addressable active pixels, or the like.

In general terms, the present invention may be described as a method of performing a fluid-material assay employing an appropriately provided (i.e., made available) computer-accessible device (note the discussion above)—preferably a pixelated matrix device, including at least one active digitally-addressable pixel having a sensor with a digitally-addressable assay site functionalized for selected fluid-assay material, with the key steps of this method including, following, of course, providing such a device, exposing the pixel's sensor assay site to such material, and in conjunction with such exposing, and employing the computer-accessible, active nature of the provided device's pixel, remotely and digitally requesting from the pixel's sensor assay site an assay-result output report.

The basic methodology further includes, in relation to the mentioned employing step, creating, relative to the sensor's assay site in the at least one pixel, a predetermined, pixel-specific electromagnetic field environment. The creation of such an environment is enabled by the type of matrix structure described both hereinbelow, and in the '174 patent application, and is specifically enabled by the presence in the described matrix pixels of one or several digitally accessible and energizable electromagnetic field-creating structure(s).

The provided device, referred to above in the just-given general description of the invention, may take on a number of different forms, not necessarily exactly the same as the device form specifically chosen herein to illustrate practice of the invention. Those skilled in the art will appreciate from the disclosure of the invention provided in this document, including the content in the mentioned currently pending, companion Regular U.S. patent application, just how to characterize a pixelated device, and its relevant features and advantages, which will be suitable for use during the performance of an assay in accordance with implementation of the methodology of the present invention.

Accordingly, the various features and advantages of the herein proposed invention methodology will become more fully apparent as the description of the setting and a typical practice of the invention are presented below in conjunction with the accompanying drawings.

DETAILED DESCRIPTION OF THE INVENTION

Definitions

Figure 1:
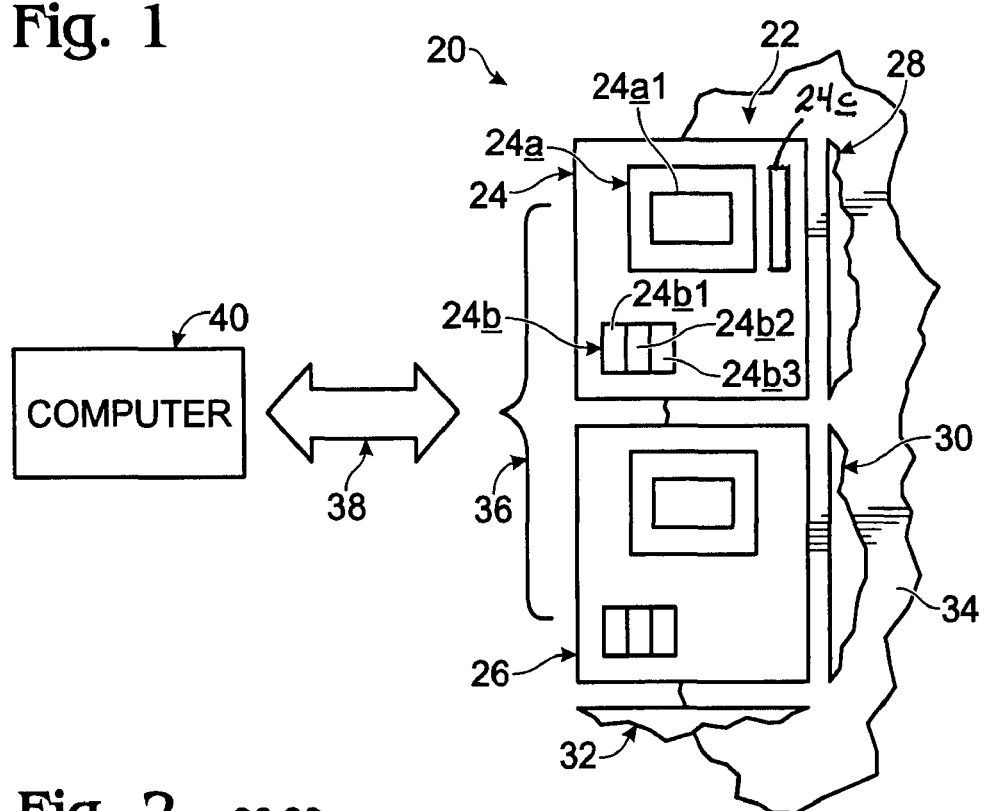
FIG. 1 is a simplified, fragmentary, block/schematic view of a portion of a digitally-addressable, pixelated, fluid-assay, active-matrix micro-structure—a device—which, when appropriately provided as part of a practice of the invention, is useable in relation to the preferred and best mode manner of practicing the present invention.

There is certain special terminology which is employed in the description and characterization of this invention—the meanings of which terminology are presented immediately hereinbelow.

The terms "active-matrix" and "active pixel" as used herein refer to a pixelated structure wherein each pixel is controlled by and in relation to some form of included, digitally-addressable electronic structure, which structure includes digitally-addressable electronic switching structure, defined by one or more electronic switching device(s), operatively associated both with also-included pixel-specific assay-sensor structure, and with pixel-bathing electromagnetic field-creating structure. Specifically, the "active" nature of an "active pixel" permits both (a) an assay-result output-report query to be posed to the pixel, and (b) accessing and energizing of the referred-to, associated pixel-bathing electromagnetic field-creating structure.

The term "bi-alternate" refers to an assay matrix structural condition wherein every other pixel in each row and column of pixels is commonly functionalized to possess response-affinity for one, specific type of a fluid-material assay. This condition effectively creates, across the entire area of such an overall matrix, two differently functionalized submatrices of pixels (what can be thought of as a two-assay, single-matrix condition).

The term "tri-alternate" refers to a similar condition, but one wherein every third pixel in each row and column is commonly functionalized for one specific type of a fluid-material assay. This condition effectively creates, across the entire area of such an overall matrix, three differently functionalized submatrices of pixels (what can be thought of as a three-assay, single-matrix condition).

Bi-alternate and tri-alternate matrices are discussed briefly in this disclosure to aid in understanding the depth of capability of the assay performance methodology of the invention.

The Drawings

Turning attention now to the drawings, we set the stage for describing the performance methodology of the present invention by describing, first, features of a "pre-assay-specific-performance", to-be-provided, computer-digitally-accessible, pixelated assay matrix structure—a device having functionalized pixels some of whose general characteristics and behaviors, as will be explained, are relevant to practice of the invention. Fundamentally, the invention is intended to be implemented in the context of using a pixelated matrix device, or the like, formed with active pixels which include assay sensors possessing assay-specific-functionalized assay sites, at least one each per pixel, that are individually, remotely, digitally addressable during the performance of an assay to obtain assay-result output readings. In an important sense, practice of the invention can take place even with an appropriate device having one such pixel.

Additionally, practice of the invention more specifically contemplates the presence, within each pixel of the type described above, of a remotely, individually digitally accessible and energizable electromagnetic field-creating structure which, during an assay, may be energized to create either a static (singular, stable) or a time-variable (staged, time variant) field condition useful variously to affect/effect associated assay-sensor responses to exposure to an assay fluid. Appropriate fields include a field of light, a field of heat, and a non-uniform electrical (or electrical potential) field.

What now immediately follows is a description of a matrix structure which meets these assay-performance-support considerations—a structure, or device, which, in accordance with certain ways of describing the present invention, is provided as a lead step for practicing the invention.

Figure 2:
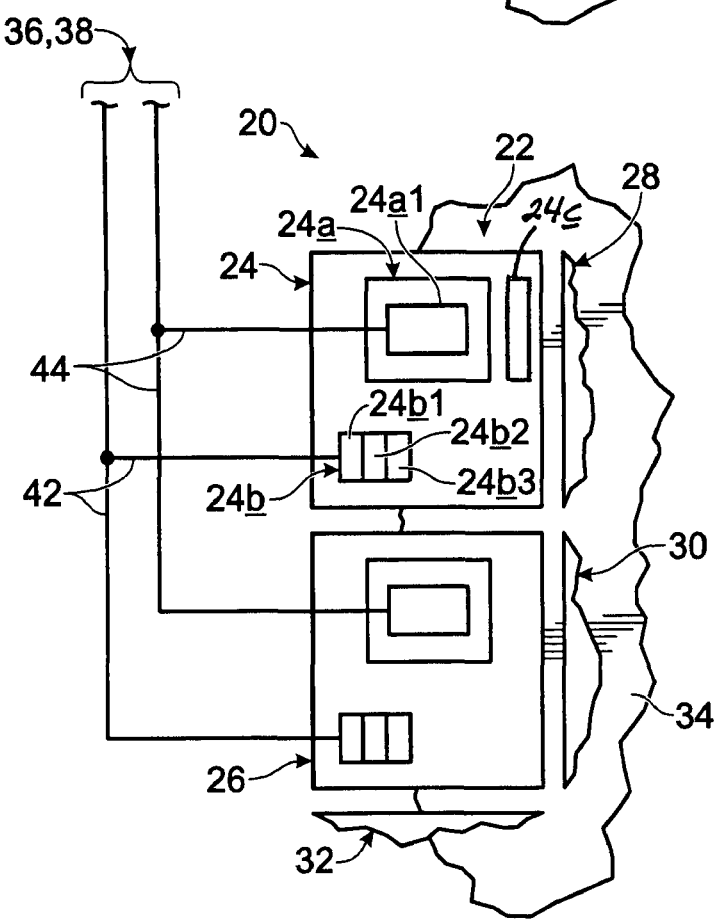
FIG. 2 is similar to FIG. 1, except that it provides a slightly more detailed view of the illustratively provided micro-structure shown in FIG. 1.

Beginning with FIGS. 1 and 2, indicated generally at 20 is a fragmentary portion of a digitally-addressable, pixelated, fluid-assay, active-matrix micro-structure which takes the form herein of a column-and-row array 22 of plural, individually, externally, digitally-addressable pixels, such as those shown at 24, 26, 28, 30, 32, formed on an appropriate supporting substrate 34 made, for example, of glass or plastic. For the purpose of illustration herein, substrate 34 will be considered to be a glass substrate.

Various known fabrication practices, not relevant to the present invention, may be utilized to create the overall structure illustrated in FIGS. 1 and 2. More information about these practices will be found in the text of the above-referred-to Ser. No. 11/827,174 patent application. Additionally, and with respect to matrix pixel structure still to be discussed herein in relation to FIGS. 5 and 6, certain portions of that structure may conveniently be formed employing an internal crystalline-structure processing approach such as that described in previously mentioned U.S. Pat. No. 7,125,451 B2.

While in no way critical to practice of the assay performance methodology of the present invention, a conveniently useable pixelated micro-structure device, such as micro-structure 20, might have lateral dimensions lying in a range of about 0.4×0.4-inches to about 2×2-inches, and might include an equal row-and-column array of pixels including a total pixel count lying in a range of about 100 to about 10,000.

Continuing with a description of what is shown in FIGS. 1 and 2, and considering an important communication pathway that is established during practice of the present invention during an assay between a pixelated device, such as matrix micro-structure 20, and a remote digital computer, a bracket 36 and a double-headed, broad arrow 38 (see FIG. 1) represent an appropriate communication/addressing connection, or path, between pixels in micro-structure 20 and such a digital computer, which is shown in block form in FIG. 1 at 40.

Regarding the illustrated operative presence of a digital computer like computer 40, it should be understood that such a computer, while "remote and external" with respect to the internal structures of the matrix pixels, per se, might actually be formed directly on-board a matrix substrate, such as substrate 34, or might truly be external to this substrate. In this context, it should be clearly understood that computer location is not any part of the present invention.

In the particular construction of micro-structure 20 which is illustrated in FIGS. 1 and 2, each of the mentioned pixels is essentially identical to each other pixel, although, as will later be explained herein, this might be different for the handling of different specific assays. This "might be different" statement is based upon an understanding, which should be made clear here, that there are various fluid-assay applications with respect to which appropriately functionally differentiated pixels might be useful in an employed, micro-structure matrix array. Some of these differentiated-pixel concepts, and how they fit with the practice methodology of the present invention, will be discussed more fully later herein.

In general terms, and using pixel 24 as an illustration to explain the basic construction of each of the pixels shown in array 22, included in pixel 24 are several, fully integrated, pixel-specific components, subcomponents, or substructures. These include, as part of more broadly inclusive pixel-specific electronic structure, (1) thin-film, digitally-addressable electronic switching structure, (2) a fully assay-functionalized, individually remotely digitally-addressable and accessible assay sensor 24a which hosts a functionalized assay site 24a$_1$, and (3) what is referred to herein as a pixel-bathing, ambient environmental, thin-film electromagnetic-field-creating structure 24b. Field-creating structure 24b, which is also remotely, or externally, individually digitally-addressable, accessible and energizable, is constructed to create, when energized, any one or more of three different kinds of pixel-bathing, assay-site-bathing, ambient, environmental electromagnetic fields in the vicinity of sensor 24a. These three different field types include a light field, a heat field, and a non-uniform electrical field.

While structure 24b, as was just mentioned, may be constructed to create one or more of these three different kinds of fields, in the micro-structure pictured in FIGS. 1 and 2, field-creating structure 24b has been designed with three field-creating subcomponents 24b$_1$, 24b$_2$ and 24b$_3$. Any one or more of these subcomponents may be computer energized to create, within pixel 24, associated assay-site bathing, ambient field conditions ("fixed-stable" or "time-variant"). Subcomponent 24b$_1$ is capable of creating a pixel-bathing light field, subcomponent 24b$_2$ a pixel-bathing heat field, and subcomponent 24b$_3$ a pixel-bathing non-uniform electrical field.

Also included in pixel 24 is an optical detector 24c. This detector, which is individually digitally addressable and accessible, may be used to "read" any fluorescence output reaction generated by assay site 24a, if and when that site is illuminated by light-field subcomponent 24b during the performance of a relevant assay, such as a DNA assay.

With regard to the active-matrix nature of micro-structure 20 which has been chosen to illustrate practice of the present invention, it will be understood that each pixel is appropriately prepared with one or more electronic switching device(s) (part of the earlier-mentioned electronic switching structure) relevant to accessing and addressing its included sensor and assay site, and accessing and energizing its included field-creating structure. Digital addressing of the electronic switching structure in a pixel is also referred to herein as "employing the active nature of the pixel".

Looking specifically at FIG. 2 in relation to a further discussion regarding how a device, such as micro-structure 20, may be connected to a fully external computer (like computer 40) during the performance of an assay in accordance with this invention, indicated generally at 42, 44 are two different communication line systems which are operatively connected, respectively, to the field-creating structures in the illustrated pixels, and to the assay sensors and assay sites shown in these pixels. The upper, fragmented ends of line systems 42, 44 in FIG. 2 are embraced by a bracket marked 36, 38, which bracket represents the previously mentioned "path" of operative connection shown to exist in FIG. 1 between micro-structure 20 and computer 40. Line system 42, under control of computer 40, is employable by this computer to access, digitally and individually, and to energize, pixel field-creating subcomponents during the performance of an assay procedure, and especially, as will be explained, during requesting and obtaining a reading-out, or outputting, of the results of a performed assay. Line system 44 directly and digitally couples, on a pixel-by-pixel, individual basis, to computer 40 assay-result output responses requested and derived (obtained) from "assay-reacted" assay sites, and from optical detector 24c. In order to avoid drawing clutter in FIG. 2, a specific line extension from line 44 to detector 24c has been omitted from this figure, although such an extension should be understood to exist.

Practice of the present invention in relation to the performance of an assay, as has been expressed already herein, involves, among other things, using an appropriately provided device having functionalized assay sites, or at least one such site, which is (are) individually digitally addressable at least for the purpose of computer-requesting, and obtaining, assay-site reaction-output information. Preferably, such a device includes a suitable plurality of functionalized assay sites, organized on, or in suitable relation to, an individually-digitally addressable and accessible assay sensor which forms part of an individually digitally addressable and accessible pixel.

Preferably also, such a device's pixels additionally include one or more electromagnetic field-creating component(s), or subcomponents, which is/are remotely, digitally accessible and energizable to create, on a pixel-specific basis, a sensor-and-assay-site-bathing field, or fields, of light, heat and/or non-uniform electrical potential.

A matrix micro-structure, such as micro-structure 20, having pixels designed with these characteristics, including one-each field-creating subcomponents covering each of the three different mentioned fields, is ideal for this purpose, and thus has been chosen for use in illustrating and describing the practice of the present invention.

Figure 3:
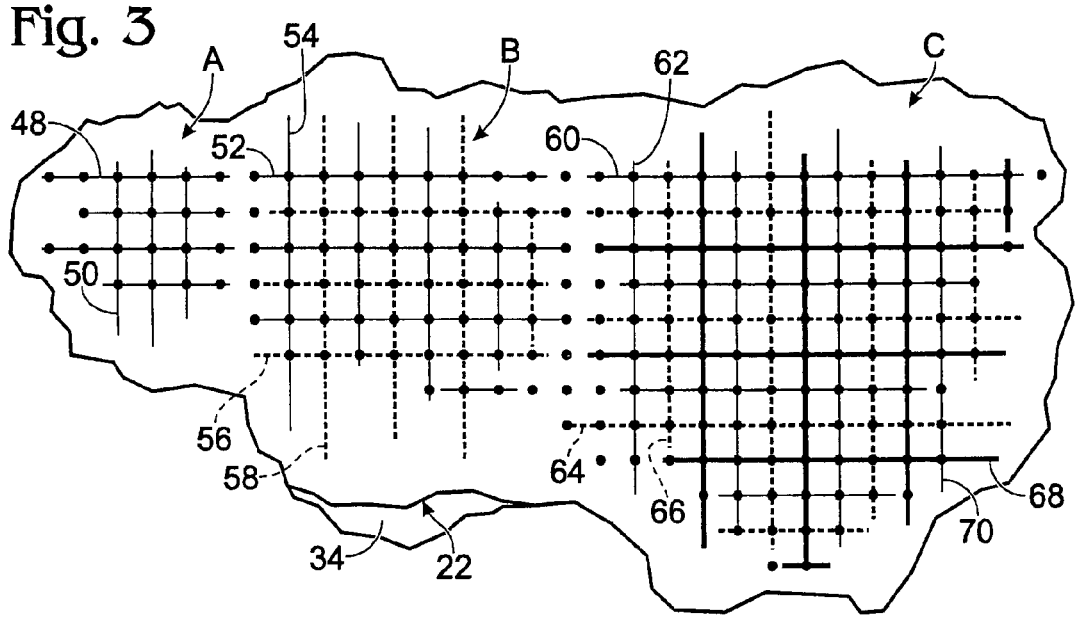
FIG. 3, which has been prepared on a somewhat larger scale than those scales employed in FIGS. 1 and 2, illustrates, schematically, different, single-matrix/device organizational ways in which fluid-assay pixels in a matrix micro-structure like that shown in FIGS. 1 and 2 may be pre-organized into different functionalized arrangements for assisting differently in different fluid-assays that are to be performed in accordance with practice of the present invention.

While the invention may very conveniently be practiced by a plural-pixelated device wherein all pixels are identically functionalized for a specific assay material, various kinds of different, functionalized-pixel-distribution patterns in a pixelated matrix device may be useful in certain assay-performance applications. FIG. 3 is provided herein to help illustrate this idea.

This figure illustrates several different such ways in which completed-matrix, fully functionalized pixels, such as the pixels in array 22, may be initially organized, and even differentiated, prior to provision/delivery of a matrix to a user for use in the practice of the present invention. To begin with, and using the construction of matrix micro-structure 20 specifically for illustration purposes the obvious, large dots, which appear throughout in a row-and-column arrangement in FIG. 3, represent the locations of next-adjacent pixels, such as the pixels in assay 22. One way of visualizing this matrix of pixels is to view the pixel arrangement as being one wherein every pixel represented by the mentioned dots is commonly functionalized to respond to a single, specific fluid-assay material.

Regions A, B, C in FIG. 3 illustrate three other, representative, possible pixel functionalization patterns (submatrix patterns) useable in the practice of the present invention.

In region A, which is but a small, or partial, region, or patch, of the overall matrix array 22 of pixels, a functionalized submatrix pattern exists, as illustrated by solid, horizontal and vertical intersecting lines, such as 48, 50, respectively, including rows and columns of next-adjacent pixels, which pixels are all commonly functionalized for a particular fluid-material assay. With this kind of an arrangement, different patches, or fragmentary areas (i.e., unified lower-pixel-count submatrices defined by side-by-side pixels), of next-adjacent pixels may be differently functionalized so that a single matrix array can be used with these kinds of patch submatrices to perform in plural, different, fluid-material assays.

In region B, intersecting, solid, horizontal and vertical lines, such as lines 52, 54, respectively, and intersecting, dashed, horizontal and vertical lines, such as lines 56, 58, respectively, illustrate two, different submatrix functionalization patterns which fit each into the category mentioned earlier herein as a bi-alternate functionalization pattern which effectively creates two, large-area-distribution submatrices within the overall matrix array 22 of pixels. These two pixel submatrices are distributed across the entire area of the overall matrix array, and are characterized by rows and columns of pixels which "sit" two pixel spacings away from one another.

FIG. C illustrates another submatrix functionalization pattern wherein intersecting, light, solid, horizontal and vertical lines, such as lines 60, 62, respectively, intersecting dashed, horizontal and vertical lines, such as lines 64, 66, respectively, and intersecting, thickened, solid, horizontal and vertical lines, such as lines 68, 70, respectively, represent what was referred to herein earlier as a tri-alternate functionalization arrangement distributed over the entire matrix array 22 of pixels—effectively dividing that array into three overlapping submatrices.

Those skilled in the art, looking at the illustrative, suggested functionalization patterns illustrated in FIG. 3, will understand how these, and perhaps other, functionalization patterns will interestingly tap the utility of the assay-performance methodology of the present invention.

Figure 4:
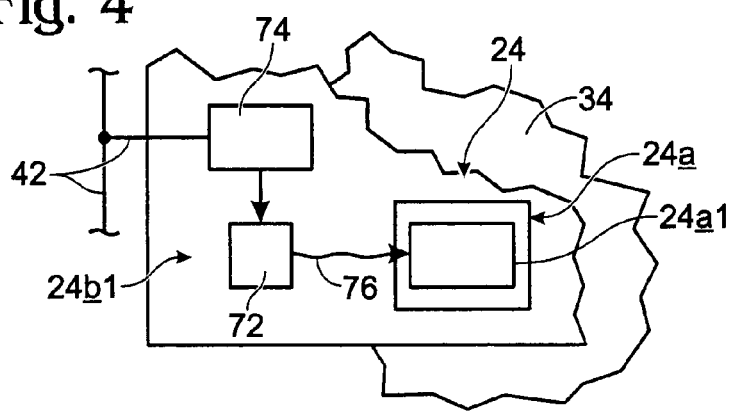
FIG. 4 is a fragmentary, block/schematic diagram showing a pixel-specific, digitally accessible, electromagnetic field-creating structure which may be employed, in the practice of the present invention, in a device like that shown in FIGS. 1 and 2, and specifically such a field-creating structure which is intended, under digitally accessible computer control, to create a pixel-specific ambient electromagnetic field environment characterized by light.

Continuing with an introductory description of matrix micro-structure 20 which has been selected to illustrate a pixelated device employable in the practice of the invention, and turning attention now to FIG. 4, this figure illustrates, schematically and fragmentarily, one style of a conventionally structured light-field-creating subcomponent. This subcomponent, with respect to what has been shown and discussed earlier herein regarding FIGS. 1 and 2, might sit at the field-creating subcomponent location which is labeled $24b_1$ in FIGS. 1 and 2.

Thus, shown specifically in FIG. 4 is an energizable, optical medium 72 which is computer-energized/switched directly by the operation of a control transistor (an electronic switching device) shown in block form at 74. This control transistor has an operative connection to previously mentioned line system 42. A sinuous arrow 76 extends from medium 72 toward prospective assay site $24a_1$ which is hosted on sensor 24a. Arrow 76 schematically pictures the creation of a field of light in the vicinity of site $24a_1$. Light from medium 72 is characterized by any suitable pre-chosen wavelength, and may be output from the medium, under computer control, at different controllable intensities (i.e., different field intensities).

Figure 5:
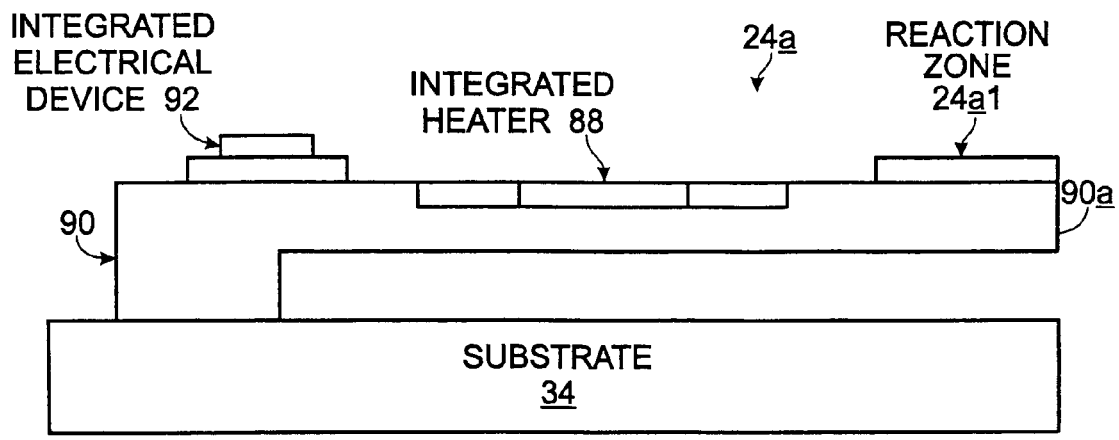
FIG. 5, which is functionally herein somewhat similar to FIG. 4, illustrates, fragmentarily, a pixel-specific, digitally accessible heat-field-creating (electromagnetic field-creating) structure that has been prepared on the body of a mechanical cantilever beam which also carries an electrical signaling structure that responds to beam deflection during an assay performance to produce a related electrical, assay-result output signal. The specific structure of this figure is utilized later herein to discuss an illustrative DNA fluid assay wherein the "provided device", a matrix device, employs assay-site-functionalized (i.e., oligonucleotide-functionalized) micro-cantilever beams, such as that shown in this figure, to respond to DNA assay fluid under environmental conditions involving the creation of pixel-specific heat fields (fixed and varying), and time-based output-result sampling.

Directing attention now to FIG. 5, here there is illustrated, schematically, an electronically (computer) switchable and intensity (temperature)-variable heat-field-creating subcomponent, which, while it may be disposed at the location generally designated $24b_2$ in FIG. 1, herein is deployed somewhat differently, and specifically, conveniently at the location of an on-sensor-24a site 88 which is formed directly on the beam 90a of a cantilever-type micro-deflection device 90 whose body has been formed utilizing the process referred to above as internal crystalline-structure processing (see U.S. Pat. No. 7,235,451 B2).

Also formed on beam 90a is an electrical signaling structure 92 which may take the form of any suitable electrical device that responds to bending in beam 90a to produce a related electrical output signal which may be coupled from the relevant pixel ultimately to an external computer, such as computer 40.

Figure 6:
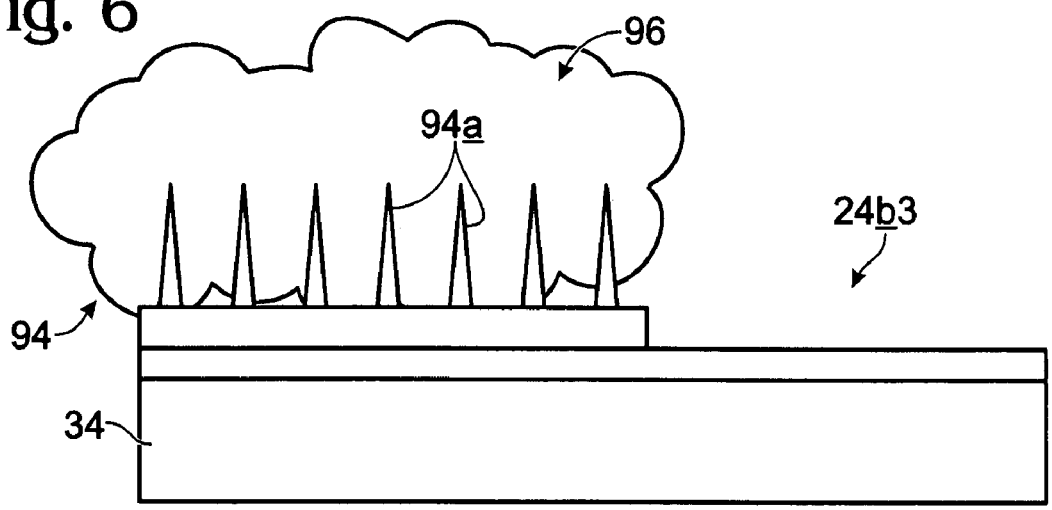
FIG. 6, which, categorically, is somewhat like FIGS. 4 and 5, provides a simplified side elevation of a pixel-specific, digitally accessible, non-uniform electrical-field-creating (electromagnetic field-creating) structure provided in a matrix micro-structure such as that pictured in FIGS. 1 and 2.

Directing attention now to FIG. 6, this figure illustrates aspects of an electronically (computer) switchable and intensity-variable, non-uniform-electrical-field-creating structure 94 which may be created within a pixel, such as within pixel 24 at the site shown at $24b_3$ in FIGS. 1 and 2. The mechanical spike structures seen in this figure have been fabricated employing the crystalline-structure-processing methodology described in the above-referred-to '451 B2 U.S. patent.

Turning attention now to FIGS. 7-11, inclusive, and recognizing that assay performance in accordance with practice of the present invention is based upon use of a suitably provided, i.e., made-available, device like micro-structure 20, these five drawing figures illustrate the basic high-level methodology of the invention which is practiceable in conjunction with such a device.

Speaking about the invention methodology, in the simplest terms, a device, like micro-structure 20 with appropriately functionalized pixels, sensors and assay sites is provided for use, and is placed in an assay-fluid environment, such as within a conventional flow-cell. A computer, like computer 40, is appropriately linked to the sensors, assay sites and field-creating structures in the device's pixels via communication/addressing path structure 36, 38, and the device's pixels are then appropriately exposed to assay-fluid in the assay environment.

In conjunction with such exposure, and typically, though not necessarily, beginning at the start of this exposure, under the control of the relevant computer, one-by-one the pixels are digitally addressed/accessed to request from their respective sensors and assay sites assay-reaction output results/information so as to obtain, collect and store if desired, and report on, that information.

This pixel-by-pixel digital addressing may also be accompanied very effectively by simultaneous accessing and energizing of pixel-specific field-creating subcomponents to produce one or more kind(s) of field(s), such as light, heat and electrical potential (or electrical gradient) fields, in the vicinities of addressed sensor assay sites in order to enhance assay-result information output. For example, with respect to a given pixel assay site, output readings may be acquired at different, computer-controlled, static, or varying, electromagnetic field conditions, such as varying field-intensity conditions, and this may also be done in a sampling fashion on a time base, thus to open opportunities for gaining multiple "axes" of assay-result output information.

Figure 7:
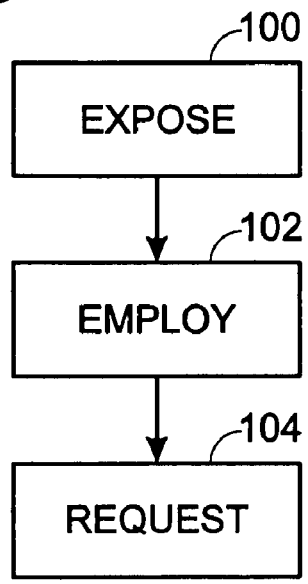
FIGS. 7-11, inclusive, provide block-schematic diagrams that illustrate different ways of viewing the methodologic practice steps of the present invention.

With this general practice description in mind, FIG. 7, which includes three blocks 100, 102, 104, illustrates one specific way of visualizing the practice of the invention. From this point of view, the invention can be expressed as being a method of performing a fluid-material assay utilizing a device including at least one active pixel having a sensor with an assay site functionalized for selected fluid-assay material, including the steps, following providing of the mentioned device, of (a) exposing the pixel's sensor assay site to such material (block 100), and in conjunction with such exposing, and (b) employing the active nature of the pixel (block 102), (c) remotely requesting from the pixel's sensor assay site an assay-result output report (block 104).

Figure 8:
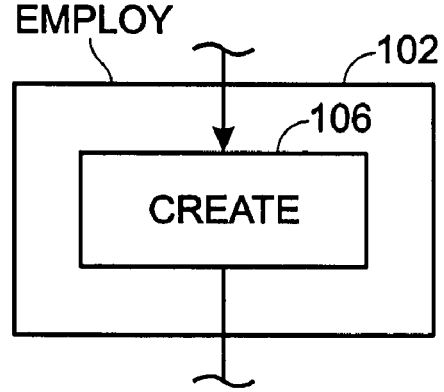

Adding, to what is shown in FIG. 7, the presence of block 106 shown in FIG. 8, the method pictured effectively in FIG. 7, and just expressed above, can be viewed as further including, in relation to the employing (block 104) step, the included, or related, or linked, step of creating, relative to the mentioned sensor's assay site (in the at least one pixel) a predetermined electromagnetic field environment (block 106).

Figure 9:
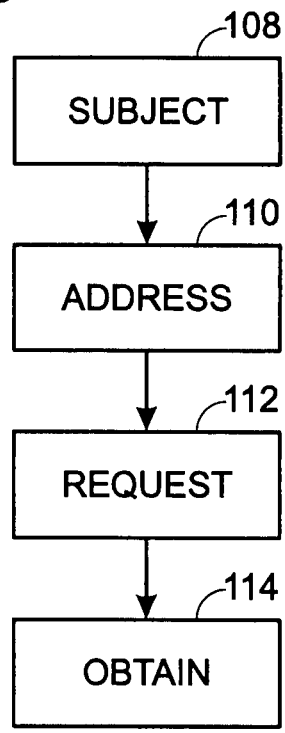

FIG. 9 shows, in four blocks 108, 110, 112, 114, several other ways of visualizing the practice of the assay performance methodology of the present invention. Looking at this figure from a point of view which focuses on blocks 108, 110, 112, the invention can be expressed as being a method for performing a fluid-material assay utilizing a pixelated assay matrix wherein each pixel possesses an assay sensor with a functionalized assay site, and is individually and remotely digitally addressable via the presence in the pixel of an active, selectively energizable electronic switching structure which is operatively connected to the sensor and its assay site. The method steps from this viewpoint include, following providing of mentioned matrix device, (a) subjecting the matrix to an environment containing assay fluid in order to effect pixel-sensor assay-site reactions (block 108), in connection with this subjecting step, (b) remotely, digitally and individually addressing selected pixel's included electronic switching structure (block 110), and (c), by that addressing step, requesting from the sensors' assay sites in the addressed pixels pixel-specific assay-result output information (block 112).

Adding block 114 into the method statement described with regard to blocks 108, 110, 112, this additional block (114) illustrates the additional step, which is a consequence of the requesting step, of obtaining from each of the selected pixels' sensors' assay sties a result-output reading of any reaction associated with that pixel's included assay-sensor assay site.

Figure 10:
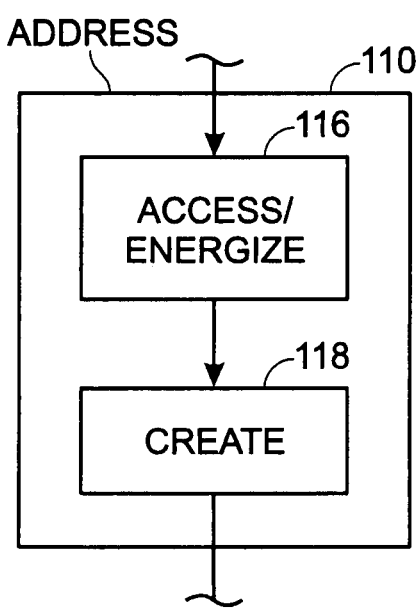

FIG. 10 in the drawings illustrates, at least partially by blocks 110, 116, 118, a further description of the invention methodology which is based upon use of an assay support device wherein each pixel further includes individually remotely and digitally accessible and energizable electromagnetic field-creating structure that is both associated with the pixel's assay sensor, and also operatively connected to the pixel's included electronic switching structure. This figure describes the methodology, as expressed above in relation to FIG. 9 in an augmented fashion by stating that the addressing step (block 110) further includes remotely, digitally and individually accessing and energizing a selected pixel's field-creating structure (block 116), and by that accessing and energizing step, creating, with respect to each selected pixel, a predetermined, pixel-specific electromagnetic field environment which exists within that pixel in operative proximity to the pixel's associated assay sensor and its associated assay site (block 118).

Figure 11:
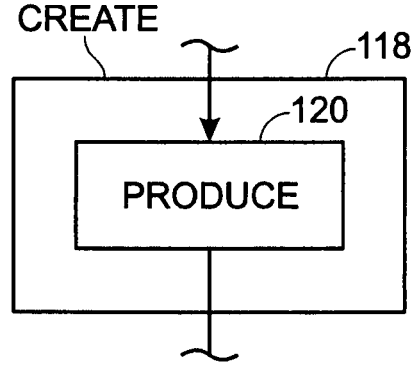

FIG. 11 illustrates with a block 120 that, from an additional perspective the just-described "creating" step includes the step of providing at least one of (a) a singular, stable, and (b) a staged, time-variant, electromagnetic field environment of the type generally mentioned in relation to the description of FIG. 10. It is also the case that this producing (block 120) step includes the selectable practice of providing different pixel-specific electromagnetic field environments with respect to different pixels.

Turning attention now to FIGS. 12-16, inclusive, and to discussion relevant thereto, these six figures are provided to illustrate issues, and resolutions thereof, involving a specific type of fluid-material assay which is performable in accordance with practice of the present invention. Recognizing that the methodology of the invention may be used with a wide variety of different fluid-material assays, this particular-assay-type illustration will serve, in conjunction with the description of the invention which has been given so far herein, to inform those generally skilled in the art about the versatile utility of the present invention.

Very specifically, the illustration now to be described relates to the performance of a DNA fluid-material assay utilizing a matrix constructed in accordance with the above-described features of micro-structure 20, and with the pixels in this micro-structure more specifically constructed in accordance with a sensor structure of the cantilever style which is illustrated in FIG. 5 in the drawings.

Even more specifically, the description of this illustrative practice of the invention will be given in the context of utilizing a computer-controlled, environmental heat field employed during the performance of an assay to enrich the obtainability of useful assay-result output information from the illustrative DNA assay. The description given now with respect to utilizing a heat-field device with respect to creating an ambient electromagnetic field in the vicinity of functionalized assay sites, should illustrate, successfully to those skilled in the art, how such a field, or others of the three different types of electromagnetic fields referred to herein, utilized either singly or in different combinations, may help to offer significantly improved output information with respect to the conducting of fluid-material assays.

Additionally, the illustration which now follows respecting a DNA-type assay will be described, at least in part, in the context of varying a heat-field condition during the performance of an assay, and additionally, in the context of taking time-spaced readings, as, for example, by a sampling technique, to include, in addition to a heat-field axis of assay-result output information, also a time-based axis of such information.

The area of, and tasks involved with, DNA assays, the issues that this assay field has raised in conventional practice, and the strikingly successful moves toward resolutions of those issues offered by the present invention, dictate why we choose this DNA assay field for a certain amount of illustrative focused discussion herein. These DNA "issues", and our invention's moves toward addressing them resolutely will serve well to convey how the practice of the present invention is shaped to deal especially and innovatively with other fluid-assay areas. Accordingly, the specific DNA assay description which now follows steps briefly into the conventional background of the performance of DNA assays, and does so in a manner, and in a context, which compares the novel utility and versatility of the present invention with prior art DNA assay practice.

In broad-brush terms, a DNA assay, aspects of which are now to be discussed, is performed utilizing a provided, pixelated matrix including appropriately functionalized sensors possessing predetermined (and not necessarily all the same) oligonucleotide probes. This matrix is placed in a suitable fluid-assay environment, such as within a conventional flow-cell, and fluid-assay material is introduced into that environment. A computer which is suitably connected operatively to the matrix's active pixels is employed, as desired, to request assay-result output information on a pixel-by-pixel basis, and also to access and energize the associated, pixel-specific heat-field-creating structures on a time-stable or time-varying basis to add interesting and highly informative output information.

We now progress a somewhat more detailed discussion regarding DNA assays through five topical zones, A-E, inclusive, identified by relevant side headings below. The texts relating to these "zones" variously blend the issues of the "past" with resolutions of the "now" offered by the present invention.

A language-term family of DNA art which appears in these texts—hybridize, hybridized and hybridization—refers to the assay-important act of affinity bonding which occurs during assay performance between a functionalized assay-site (an oligonucleotide probe in the DNA world) and an assay-fluid component (a DNA or RNA molecule, referred to as a target).

A. Functionalized Assay Site

Currently, and here discussing conventional heating-based DNA assays, all oligonucleotide probes employed in DNA-assay arrays can only be hybridized at substantially the same temperature, since each such whole array is heated simultaneously during assay performance. Thus, to obtain optimum array performance in the past, it has been essential to design oligonucleotide probes with melting temperatures that lie within a relatively narrow melt-temperature window, usually of about 5° C. This requirement for substantially uniform probe melting temperatures reduces assay flexibility, and puts serious constraints on probe-design algorithms.

Individual heating devices positioned in close vicinity to probes, such as the heat-field-creating structures proposed herein for use in the practice of our present invention, will enable one to hybridize each probe at a different temperature. Thus, instead of initially preparing, within an array of probes, probes with melting temperatures that lie within narrow temperature windows, it becomes possible to utilize individual hybridization temperatures matched to melting temperatures for different probes.

Recognizing that practice of the present invention contemplates, in part, pre-assay-per-se-performance provision of a device prepared in advance to have suitably functionalized assay sites associated with pixel-specific assay sensors, one intending to perform a particular DNA assay with such differently melt-temperature functionalized probes may readily specify an appropriate matrix functionalization "pattern" designed to accommodate this requirement. While a matrix supplier may choose different ways to meet such a request, one very effective way for doing so is described in U.S. patent application Ser. No. 11/827,173 filed on Jul. 10, 2007 for "Micro-Pixelated Fluid-Assay Structure With On-Board, Addressable, Pixel-Specific Functionalization". The full disclosure content of that patent application is hereby incorporated herein by reference.

This option of using melt-temperature differentiation is very significant for some DNA-assay applications where, for example, probes are designed for really short sequences, and there is no easy opportunity for probe selection. A typical example of such an application involves one aimed at the detection of micro-RNA expression important for cancer research.

B. Assay Confidence

A major issue relating to conventional DNA-assay arrays is so-called background signal associated with non-specific binding of labeled targets. Such binding can be caused by cross-hybridization of targets with similar heterologous probes, and by random non-specific attachment of targets to probes distributed over a matrix array surface. Cross-hybridization to heterologous probes depends on hybridization temperature, and can be decreased by precise temperature adjustment in the vicinity of probes. In addition, non-specific binding differs from specific target-probe hybridization in terms of temperature dependence, and these two processes can be clearly distinguished by utilizing the "additional information axis" capability of the present invention, thereby obtaining a temperature-to-binding dependence category of output information. A detected binding signal that does not match a profile for the specific, intended interaction can be considered to be a false positive signal.

The ability, thus, to perform hybridization of a target DNA or RNA molecule with multiple identical probes at different temperatures, as is readily accommodated by the present invention, allows one to characterize the temperature dependence of target hybridization. This dependence can be used as a fingerprint approach for specific target-probe interactions, and it can be used to discriminate false positive signals on a matrix array. For so-called SNP (Single Nucleotide Polymorphism) assays, those skilled in the relevant art will appreciate that this approach will result in robust distinguishing between mutant and wild-type alleles.

C. SNP Assay

Figure 12:
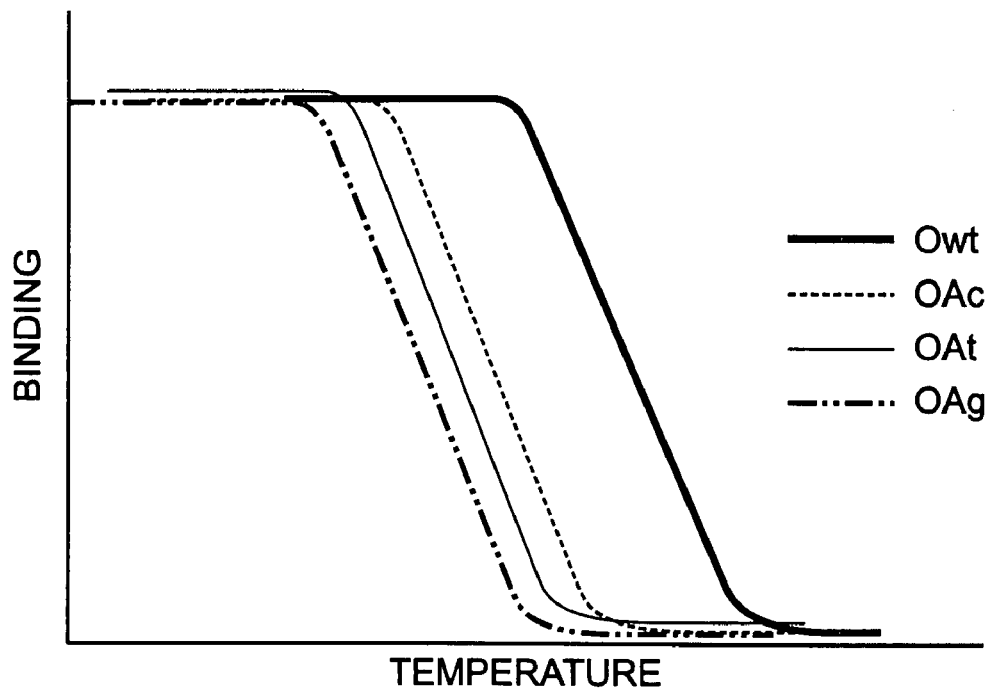
FIGS. 12-16, inclusive, help to describe various aspects of the above-mentioned, illustrative DNA fluid assay, with respect to which a controlled heat field may be employed, and also time sampling may be used, to furnish different axes of assay-result output information obtainable from practice of the present invention. This DNA-assay illustration provides a good basis for understanding the versatile utility of the invention with respect to both biologic and other specific types of fluid assays where electromagnetic-field axes, and time axes, of output information may similarly be obtained.

SNP discovery and detection is a very important area of DNA assay applications in basic research and clinical diagnostics. The ability to distinguish the so-called wild-type DNA target molecule from one that has a single sequence mismatch is based on different target-to-probe binding behaviors at different temperatures. For example, FIG. 12 shows the typical expected temperature dependence of target-to-probe binding for a wild-type DNA (0 wt), and for three, corresponding mismatches 0 At, 0 Ac, and 0 Ag.

This theoretical plot demonstrates that a clear difference in binding for so-called wild-types and mismatches can only be obtained in a relatively broad, rather than in a very narrow, temperature range. If a whole matrix array of probes (of functionalized assay sites) is heated simultaneously, it will thus most probably be quite difficult to achieve optimum distinction for all probes. Each set of probes may require a certain temperature range that is different from those required by other sets of probes.

Figure 13:
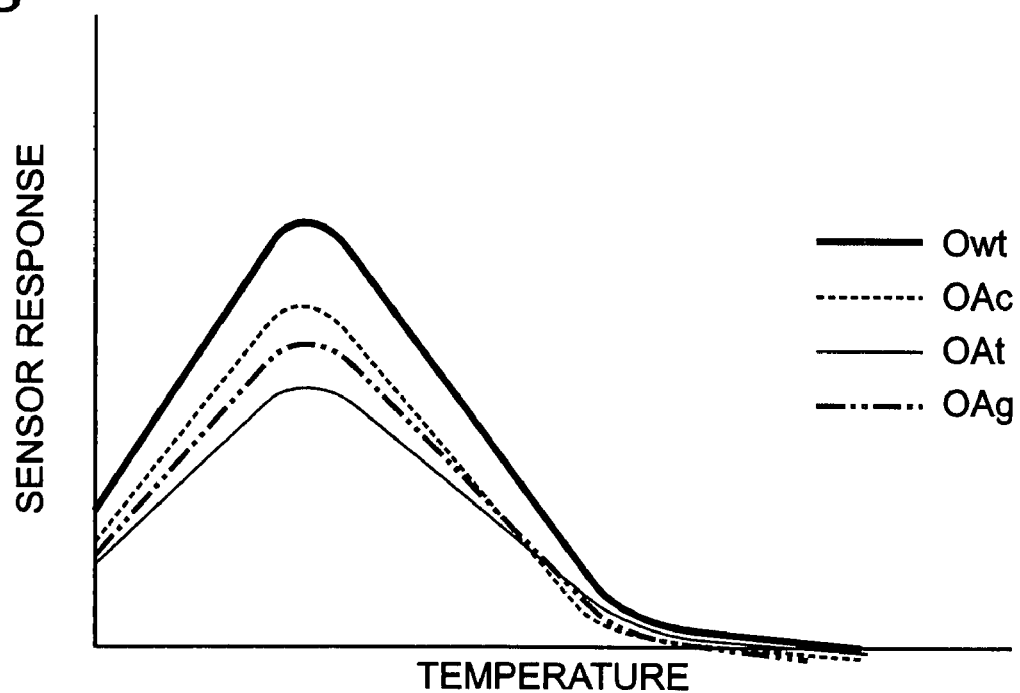

Generally, the temperature-dependence profiles of target-probe hybridizations, if acquired in accordance with the practice of the present invention where different individual probes essentially "function" at different predetermined temperatures, can readily be read to distinguish not only between wild-type oligonucleotides and mismatches, but also between mismatches. FIG. 13, which illustrates this, shows representative temperature-to-binding-dependence curves, or plots, that would be obtained typically by using an array of numerous oligonucleotide assay probes for such a set of targets where different probes in this array are designed for, and are hybridized at, different temperatures. Temperature variation in this setting will typically be performed independently for groups of assay sites (probes) that have been commonly functionalized to possess replicates of the same probe. Thus FIG. 13 indicates that the measurement (and plotting) of temperature-to-binding dependence will permit discrimination between the wild type and mismatching sequences as well as among different mismatches.

Assay-site-specific sets of heating elements, as proposed for use in certain pixelated assay devices provided in conjunction with practice of the present invention, will contribute to a way to perform hybridizations at different temperatures for individual probes within one pixelated matrix array, and will result in accommodating the obtaining of temperature-to-binding profiles, like those pictured in FIG. 13, in a single test assay.

Figure 14A:
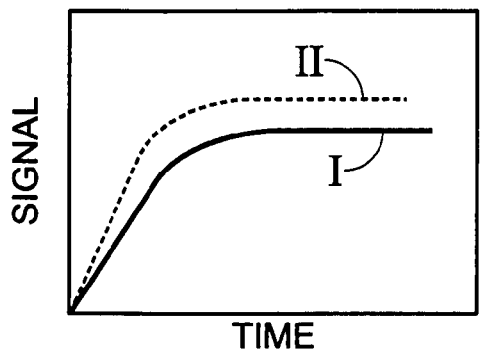
Figure 14B:
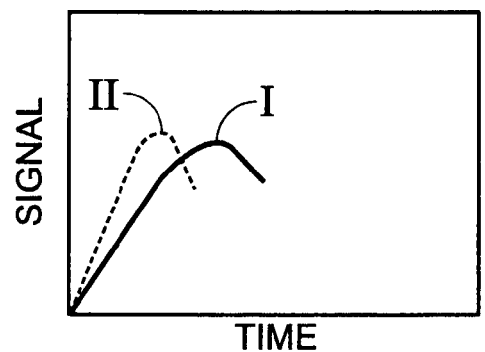
Figure 15:
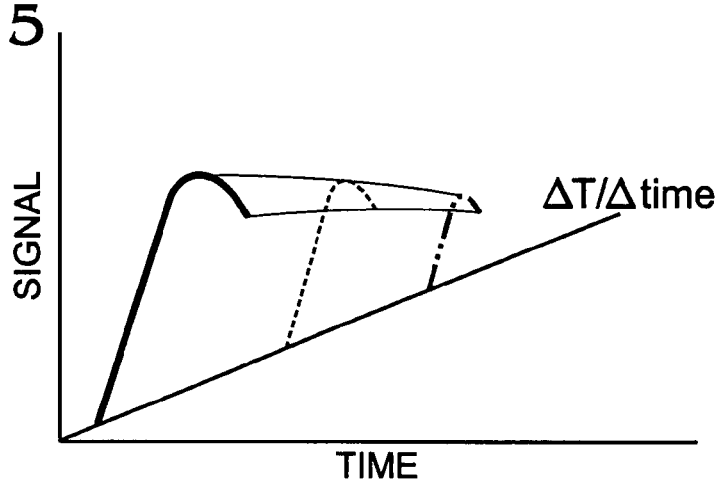
Figure 16:
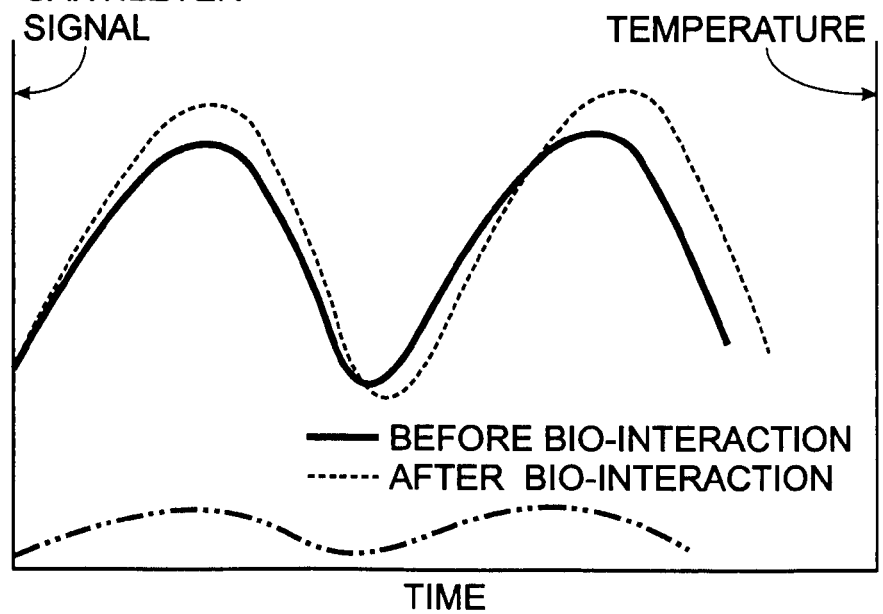

D. Target-to-Probe Hybridization at Time-Varying Temperatures Accompanied with Real Time, Time-Axis Detection Real-time, time-axis detection that is performed by a sensor and its functionalized assay site at time-varying hybridization temperatures allows one to obtain a unique individual pattern for each target-to-probe interaction. FIG. 14A shows a typical, expected hybridization signal for two different target and probe pairs at a constant temperature. Saturation of the signal, illustrated in this figure, corresponds to the stage where hybridization equilibrium is achieved. If the two, pictured target-probe pairs I and II have a closely similar sequence (for example, in the case of an SNP assay), the plots obtained for pairs I and II are difficult to distinguish. If, however, hybridization is performed at time-varying temperatures (FIG. 14B), the resultant signal-to-time dependence plots have more complicated and perceivably different patterns. Such temperature variations (field-intensity variations/variants) are contemplated, of course, as a useful possibility in the practice of the present invention.

At low temperatures, target-to-probe hybridization will cause an increase in a detected binding signal. When the hybridization temperature exceeds the melting point for the subject target-probe pair, hybrids start to denature, causing a corresponding decrease in signal (see generally the right-side portion of FIG. 13). Thus, real-time detection of hybridization signals at time-varying temperatures can provide unique and readily distinguishable individual characteristics for each target-probe pair. For example, the upper "turn points" of plots I and II in FIG. 14B can be used to distinguish highly similar target sequences.

Temperature time varying can also be performed independently for several sensing elements (assay sites) that contain (have been functionalized to contain) replicates of the same probe. In such a case, the rate of temperature increase ($\Delta T/\Delta$ time) is different for different replicates. Thus, several signal-to-time dependence plots can be obtained for a particular target-probe pair (see FIG. 15). These plots form a virtual three-dimensional surface that is a fingerprint characteristic of an analyzed target-probe pair.

These temperature time-varying illustrations not only describe herein a temperature-axis method for performing a DNA assay, they also illustrate that characteristic of the present invention which enables the obtaining of assay-result output information on a time-based axis, as by sampling on such an axis.

E. Active Thermal Oscillation of a Cantilever Transducer

Commonly, where a cantilever-style sensor is employed, a relevant cantilever "transducer signal" is associated with detection of a cantilever deflection that is caused by a surface-tension change due to bio-interactions occurring on the cantilever surface at the location of a functionalized assay site. The ability, offered during practice of the present invention, to vary, over time, the temperature in the cantilever vicinity allows for generation of a changing cantilever deflection. Thus, a "temperature oscillation" (see the light-colored, lower solid line in FIG. 16 in relation to the temperature-level axis which appears on the right side of this figure) results in a related, basic oscillation of cantilever response (see the darker, upper solid line in FIG. 16 in relation to the signal-level axis which appears on the left side of this figure). Binding of bio-molecules to such a cantilever surface at the location of a functionalized assay site changes the signal-axis pattern of the cantilever oscillation (see the dashed line in FIG. 16). Thus, such an oscillation pattern change can be used for quantification of bio-molecules which are assay-site-captured during an assay.

From the above-discussion regarding the performing of a representative DNA assay wherein pixel-specific electromagnetic-field heat plays a role, and from the invention description given herein, it will be evident to those skilled in the art how other performance approaches may be employed for conducting a DNA assay. For example, instead of using a cantilever-type sensor in a device provided for the purpose of performing such an assay, one could alternatively employ a device having pixels featuring non-cantilever, functionalized assay sites, and offering the use of a pixel-specific light field, and pixel-specific optical detection, to query an assay-site for reaction-output information during a DNA assay. Above-mentioned patent application Ser. No. 11/827,173 fully describes this kind of DNA-assay approach.

Further evident to those skilled in the art will be the fact that more than a single type of electromagnetic field may be employed in the practice of a DNA assay. For example, combined fields of light and heat, or other plural-combined fields, may be utilized.

The DNA-specific-assay discussion just presented above will also arm those skilled in the art with a clear understanding of how various non-DNA fluid-material assays may be conducted using the methodology proposed by the present invention.

Accordingly, a preferred and best mode manner of practicing the present invention, and several modifications thereof, have been illustrated and described herein. From these disclosures, those skilled in the relevant art will appreciate the numerous advances and advantages which are offered by the invention in relation to the carrying out of various different types of fluid-material assays. Also, those so skilled will additionally appreciate that other, currently unidentified variations and modifications may come to their minds, and may be included in the practice of the invention, with these variations and modifications being clearly implementable without departing from the spirit of the invention as set forth herein in the several claims to invention.

We claim:

1. An active, thin-film-transistor-based matrix method for performing a DNA fluid-material assay comprising
   providing for use in the performance of such an assay a single, common substrate having a single, commonly-pixel-shared face on which is formed a plural, electronically-active-pixel, thin-film-transistor-based matrix assay of plural pixels, wherein each pixel on the commonly shared face possesses within it
   (a) an assay site affinity-functionalized with a DNA oligonucleotide probe prepared to respond to a selected DNA fluid-assay material, and
   (b) disposed operatively and laterally adjacent the assay site and probe, and also on the commonly-pixel-shared face, an energizable, light-field-creating structure including (1) a switching transistor, and (2) a light-field-illuminating optical medium operatively connected to, and energizable by operation of, the transistor, the optical medium being structured, when energized by operation of the transistor, (a) to create, from, and adjacent, its location on the shared face, an (b) to illuminate and bathe the assay site and the probe with, an ambient light field which is operable to assist in the requesting of an assay-result response from the assay site, subjecting the matrix to an environment containing assay fluid in order to effect assay-site assay reactions, in conjunction with said subjecting, remotely, digitally, independently and individually addressing, and thereby activating and energizing, respectively, selected pixels' included switching transistors and light-field-creating structures, by said energizing initiating the creation of respectively associated, pixel-specific light fields, bathing the respective associated functionalized assay sites with th light fields created by the associated light-field-creating structures, and by said bathing, requesting from the bathed assay sites pixel-specific assay-result output information.

2. The method of claim 1, wherein said initiating involves producing at least one of (a) a singular, stable, and (b) a staged, time-variant, light-field environment in the vicinity of the associated assay site.

3. The method of claim 1, wherein said initiating involves producing different pixel-specific light-field environments with resect to different pixels.

4. The method of claim 3, wherein said producing involves, more specifically, producing, with respect to each of such different pixels, at least one of (a) a singular stable, and (b) a staged, time-variant, light-field environment in the vicinity of the associated assay site.

* * * * *

UNITED STATES PATENT AND TRADEMARK OFFICE
CERTIFICATE OF CORRECTION

| | | |
|---|---|---|
| PATENT NO. | : 8,232,109 B2 | |
| APPLICATION NO. | : 11/888491 | |
| DATED | : July 31, 2012 | |
| INVENTOR(S) | : John W. Hartzell et al. | |

It is certified that error appears in the above-identified patent and that said Letters Patent is hereby corrected as shown below:

Column 15, line 2, "an" should read --and--.
Column 15, line 16, "th" should read --the--.

Signed and Sealed this
Eighteenth Day of September, 2012

David J. Kappos
*Director of the United States Patent and Trademark Office*